United States Patent
Teodoro et al.

(10) Patent No.: US 9,456,541 B2
(45) Date of Patent: Oct. 4, 2016

(54) EMBRYO INSERTION AND METHOD

(71) Applicant: WEYERHAEUSER NR COMPANY, Federal Way, WA (US)

(72) Inventors: Michael W. Teodoro, Tacoma, WA (US); Frederick T. Rubatino, Tacoma, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 112 days.

(21) Appl. No.: 13/714,168

(22) Filed: Dec. 13, 2012

(65) Prior Publication Data

US 2013/0167437 A1    Jul. 4, 2013

Related U.S. Application Data

(60) Provisional application No. 61/581,832, filed on Dec. 30, 2011.

(51) Int. Cl.
| | |
|---|---|
| *A01C 1/00* | (2006.01) |
| *A01C 1/06* | (2006.01) |
| *A01H 4/00* | (2006.01) |

(52) U.S. Cl.
CPC .............. *A01C 1/06* (2013.01); *A01H 4/006* (2013.01)

(58) Field of Classification Search
CPC ............ A01C 1/00; A01C 1/06; A01C 1/04; A01C 1/046; A01C 2001/048; A01H 4/00; A01H 4/006; A01G 1/001; A01G 7/00
USPC ...................... 47/57.6, 58.1 SE, 58.1 R, 65
See application file for complete search history.

(56) References Cited

U.S. PATENT DOCUMENTS

| | | | | |
|---|---|---|---|---|
| 3,690,034 | A | * | 9/1972 | Knapp ........................ 47/57.6 |
| 3,848,772 | A | * | 11/1974 | Aanestad et al. ............. 222/617 |
| 3,960,292 | A | * | 6/1976 | Knapp ......................... 221/211 |
| 4,808,430 | A | * | 2/1989 | Kouno ............................ 427/4 |
| 5,377,727 | A | | 1/1995 | Ueda et al. |
| 5,701,699 | A | | 12/1997 | Carlson et al. |
| 6,048,571 | A | * | 4/2000 | Kohno et al. ..................... 427/4 |
| 6,209,259 | B1 | * | 4/2001 | Madigan et al. ............. 47/57.6 |
| 6,684,564 | B1 | | 2/2004 | Hirahara |
| 6,912,969 | B2 | * | 7/2005 | Nakatsukasa ............ A01C 1/06 118/13 |
| 7,207,139 | B2 | | 4/2007 | McKinnis et al. |
| 7,603,807 | B2 | | 10/2009 | McKinnis et al. |

(Continued)

OTHER PUBLICATIONS

U.S. Appl. No. 61/359,917, filed Jun. 30, 2010, Rubatino et al.
U.S. Appl. No. 61/359,930, filed Jun. 30, 2010, Rubatino et al.
U.S. Appl. No. 61/387,244, filed Sep. 28, 2010, Hartle.

*Primary Examiner* — Joshua Huson
(74) *Attorney, Agent, or Firm* — Perkins Coie LLP

(57) ABSTRACT

The present disclosure is directed generally towards to embryo insertion systems and methods for use with manufactured seeds. In some embodiments, embryo insertion systems according to the disclosure include an embryo delivery assembly and a fill material deposit assembly. The embryo delivery assembly may include an insertion member, a release assistance member, and a fill material deposit assembly. The fill material deposit assembly may include a fill material containment device, a fill material conveyance device, and, optionally, a fill material separation device. Further aspects of the disclosure relate to methods for operating embryo insertion systems according to embodiments of the disclosure to enable simultaneous embryo insertion and fill material delivery.

9 Claims, 12 Drawing Sheets

(56) References Cited

U.S. PATENT DOCUMENTS

| | | | |
|---|---|---|---|
| 2003/0051397 A1* | 3/2003 | Hirahara | A01H 4/006 47/57.6 |
| 2004/0118340 A1* | 6/2004 | Nakatsukasa | A01C 1/06 118/300 |
| 2005/0013892 A1 | 1/2005 | Downs et al. | |
| 2005/0133528 A1 | 6/2005 | Hirahara | |
| 2006/0032121 A1 | 2/2006 | Hirahara | |
| 2006/0048248 A1 | 3/2006 | Depperman | |
| 2009/0090050 A1* | 4/2009 | Hartle et al. | 47/57.6 |
| 2011/0072716 A1 | 3/2011 | Hartle et al. | |
| 2012/0000125 A1* | 1/2012 | Rubatino | B25J 15/0616 47/57.6 |
| 2012/0003074 A1* | 1/2012 | Rubatino | A01H 4/006 414/752.1 |
| 2013/0000192 A1* | 1/2013 | Hartle | A01H 4/006 47/57.6 |
| 2013/0007921 A1* | 1/2013 | Hartle | A01H 4/006 800/298 |

* cited by examiner

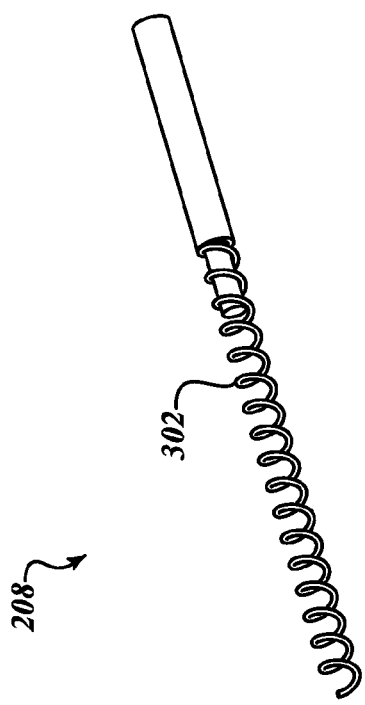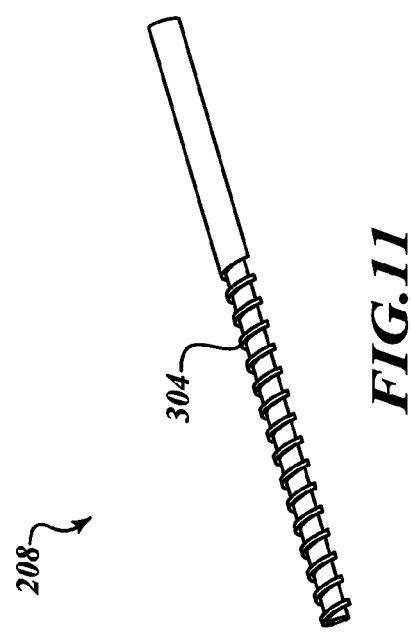
FIG.10
FIG.11

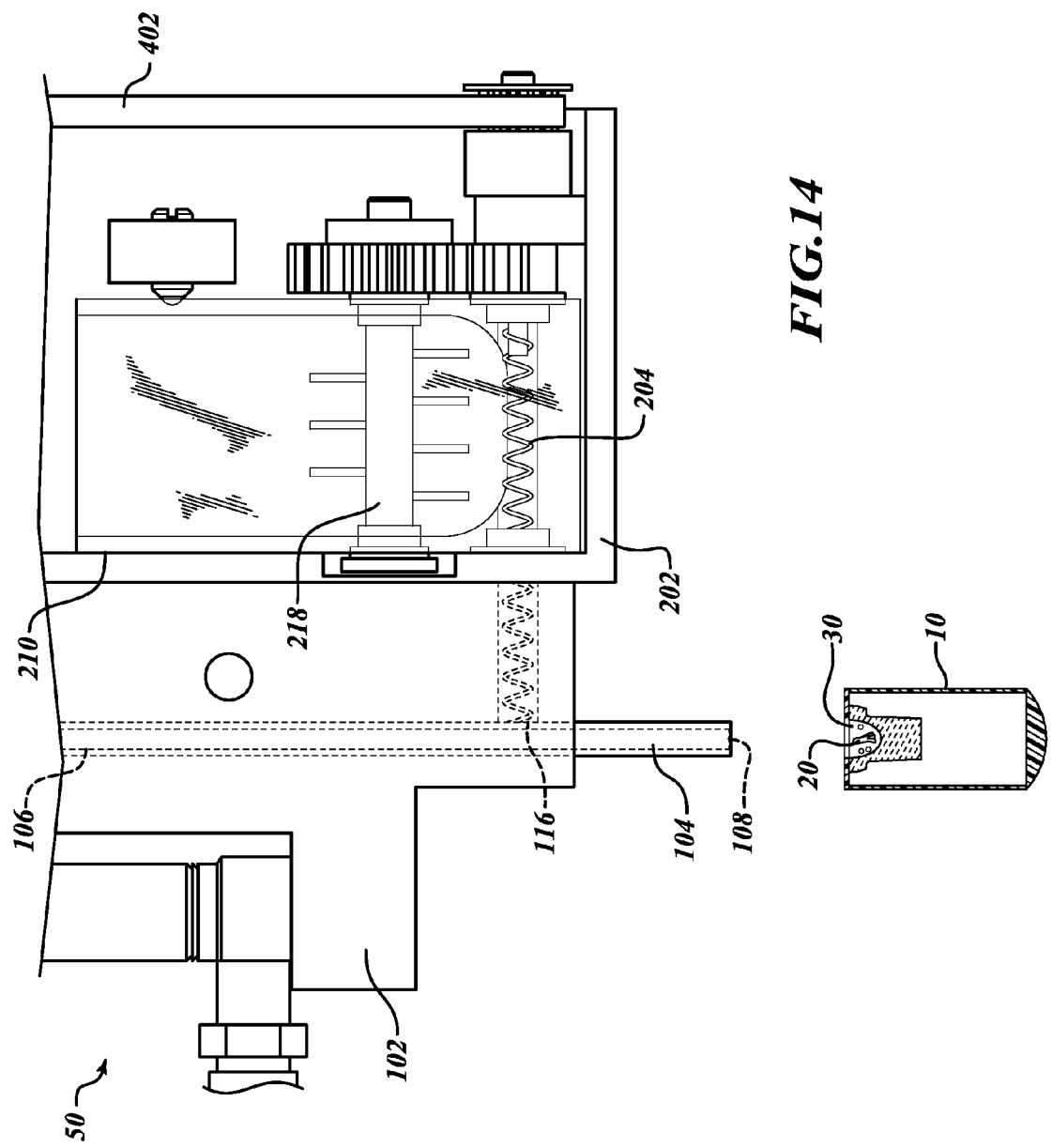

EMBRYO INSERTION AND METHOD

CROSS-REFERENCE TO RELATED APPLICATION

This application is entitled to and claims the benefit of priority under 35 U.S.C. §119 from U.S. Provisional Application Ser. No. 61/581,832 filed Dec. 30, 2011 Patent, and titled "EMBRYO INSERTION SYSTEM AND METHOD," the contents of which are incorporated herein by reference.

TECHNICAL FIELD

The present disclosure is directed generally to material handling systems, and particularly to embryo insertion systems and methods for use with manufactured seeds.

BACKGROUND

Modern agriculture, including silviculture, often requires planting of large numbers of substantially identical plants that are genetically tailored to grow optimally in a particular locale or to possess certain other desirable traits. Production of new plants by sexual reproduction can be slow and is often subject to genetic events resulting in variable traits in its progeny. As a result, asexual propagation has been shown to yield large numbers of genetically identical embryos for some species. Such embryos are typically further cultured under laboratory conditions until they mature into an autotrophic "seedling" state characterized by an ability to produce their own food via photosynthesis, to resist desiccation, to produce roots able to penetrate soil, and to fend off soil microorganisms.

Researchers have experimented in asexual propagation with the production of artificial seeds known as "manufactured seeds." Manufactured seeds typically include the following components: a seed shell, a synthetic gametophyte, and a plant embryo. A manufactured seed that does not contain a plant embryo is known in the industry as a "seed blank." The seed blank is typically a cylindrical capsule made from biodegradable plastic having an open end and a closed end. Manufactured seeds are produced by placing the synthetic gametophyte within the seed shell such that it substantially fills the interior of the seed shell. A longitudinally extending hard porous insert, known in the industry as a "cotyledon restraint," may be centrally located within the synthetic gametophyte. The cotyledon restraint includes a centrally located cavity extending partially through its length and is sized to receive the plant embryo. The plant embryo is approximately 4 to 7 millimeters in length and roughly 0.5 millimeters in diameter. The shape of the plant embryo is somewhat cylindrical, but is also irregular in cross-section and varies in diameter along its length. The plant embryo may contain both a radicle (or root) end and a cotyledon end. The plant embryo is deposited into cavity of the cotyledon restraint oriented so that the cotyledon end is inserted first. Subsequently, the plant embryo is typically sealed within the seed shell using at least one end seal.

Numerous types of plant embryo delivery systems have been used to transfer the plant embryo through the manufactured seed production line. Examples of such systems include U.S. Pat. No. 6,684,564, U.S. Pat. No. 7,207,139, and U.S. Pat. No. 7,603,807, all of which are hereby incorporated by reference. Although known systems have been effective in transporting plant embryos, problems are often encountered. For example, in some applications, embryos are hydrated to prevent damage from desiccation. These moist and sticky embryos often remain attached to plant embryo delivery systems and may be damaged during removal attempts. Even if the embryo is not damaged, sticking can also cause improper orientation or placement in the seed shell. Either scenario results in the possibility of wasting viable embryos, which is costly in commercial applications. Accordingly, there is a need in the industry to develop new systems and methods for embryo insertion into manufactured seeds.

SUMMARY

The following summary is provided for the benefit of the reader only and is not intended to limit in any way the invention as set forth by the claims. The present disclosure is directed generally towards to embryo insertion systems and methods for use with manufactured seeds.

In some embodiments, embryo insertion systems according to the disclosure include an embryo delivery assembly and a fill material deposit assembly. The embryo delivery assembly may include an insertion member, a release assistance member, and a fill material deposit assembly. The fill material deposit assembly may include a fill material containment device, a fill material conveyance device, and optionally, a fill material separation device. Further aspects of the disclosure relate to methods for operating embryo insertion systems according to embodiments of the disclosure to enable simultaneous embryo insertion and fill material delivery.

BRIEF DESCRIPTION OF THE DRAWINGS

The present disclosure is better understood by reading the following description of non-limitative embodiments with reference to the attached drawings wherein like parts of each of the figures are identified by the same reference characters, and are briefly described as follows:

FIGS. 10 and 11 are isometric views of conveyor devices according to embodiments of the disclosure; and FIGS. 12-14 are side views of embryo insertion systems according to embodiments of the disclosure in various stages of operation.

DETAILED DESCRIPTION

The present disclosure describes to embryo insertion systems and methods for use with manufactured seeds. Certain specific details are set forth in the following description and FIGS. 1-14 to provide a thorough understanding of various embodiments of the disclosure. Well-known structures, systems, and methods often associated with such systems have not been shown or described in detail to avoid unnecessarily obscuring the description of various embodiments of the disclosure. In addition, those of ordinary skill in the relevant art will understand that additional embodiments of the disclosure may be practiced without several of the details described below.

In this disclosure, the term "plant embryo" is used to describe part of a seed consisting of precursor tissues for the leaves, stem, and root, as well as one or more cotyledons. The disclosure is not intended to be limited to any particular type of seed. For example, embodiments according to the disclosure are suitable for use with plant embryos related to agricultural seeds, seeds for producing trees, or any other type of seed.

Figure 1:
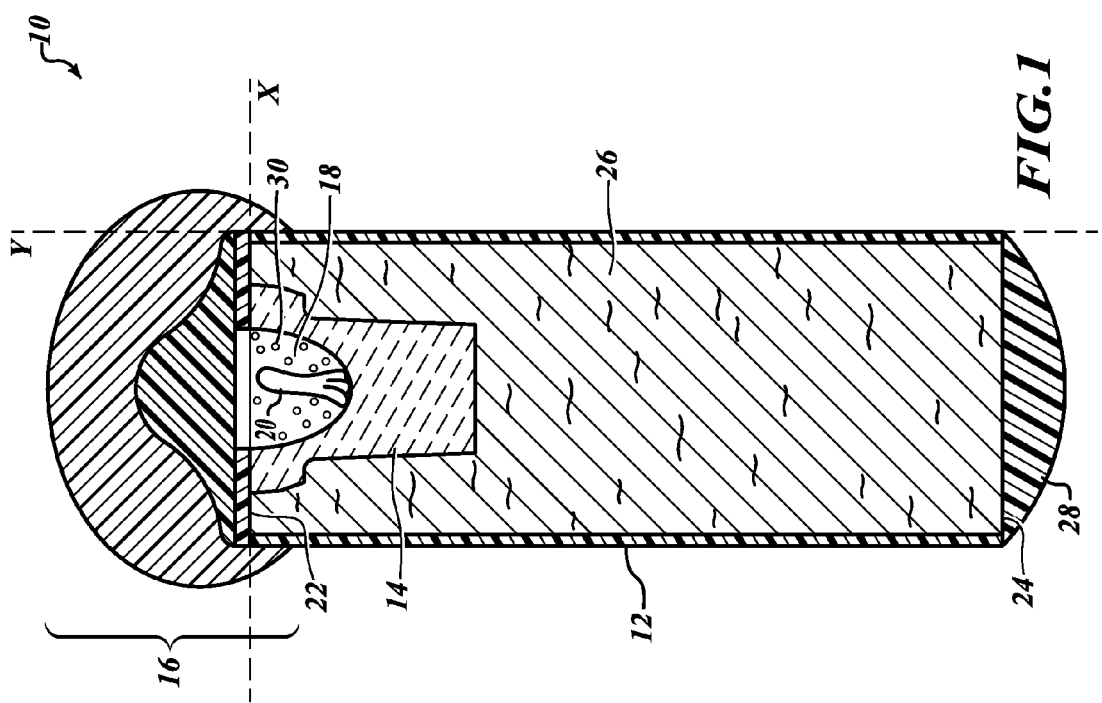
FIG. 1 is side cross-sectional planar view of a manufactured seed having a packing material in accordance with certain aspects of the present disclosure.

FIG. 1 is a manufactured seed 10 arranged on a coordinate system comprising an x-axis (X), a y-axis (Y), and a z-axis (Z). Manufactured seeds 10 according to embodiments of the disclosure generally include the following components: a seed shell 12, a shoot restraint 14 disposed within the seed shell 12, and a seal assembly 16 (e.g., a live end seal). The shoot restraint 14 includes a longitudinally extending cavity 18 that extends at least partially through the length of the shoot restraint 14. A plant embryo 20 may be disposed in the cavity 18.

As shown in FIG. 1, the seed shell 12 has an open end 22 (e.g., a live end) and a closed end 24 (e.g., a dead end seal). The closed end 24 may be sealed using an end seal 28 or any other means known to a person of ordinary skill in the art. The seed shell 12 may be configured to house a nutritive medium 26 that is in functional contact with the embryo 20. Nutritive media 26 according to the disclosure may include a substance that causes the media to be a semi-solid or have a congealed consistency under normal environmental conditions. Suitable nutritive media 26 are described, for example, in U.S. Pat. No. 5,701,699 and U.S. Patent Application Ser. No. 61/387,244, the disclosures of which are hereby incorporated by reference. Further, other types of nutritive media 26 that would be suitable to a person of ordinary skill in the art are foreseen to be within the scope of this disclosure.

A fill material 30 may be disposed in the cavity 18 of the shoot restraint 14. In some embodiments the fill material 30 is a powder. In some embodiments, the fill material 30 is an adsorbent, such as charcoal, resins, zeolites, alumina, clay, diatomaceous earth, talcum powder, and silica gel. Examples of suitable fill materials 30 are described, for example, in U.S. Published Patent Application No. 20090090050A1, the contents of which are hereby incorporated by reference. Fill materials 30 according to the disclosure may be nutritive or non-nutritive (e.g., release agents). Further, other types of fill materials 30 that would be suitable to a person of ordinary skill in the art are foreseen to be within the scope of this disclosure.

Figure 2:
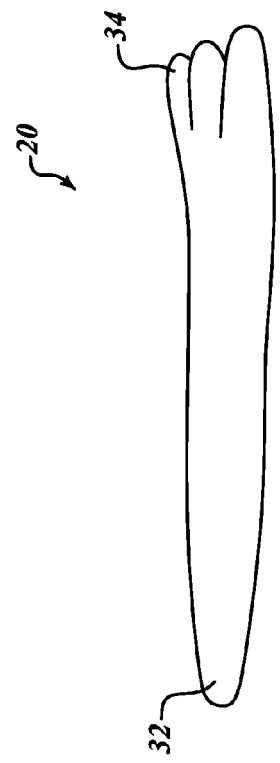
FIG. 2 is a side view of a plant embryo suitable for use with embodiments according to the disclosure.

FIG. 2 is a more detailed view of the plant embryo 20 shown in FIG. 1. The plant embryo 20 is shown having a radicle (or root) end 32 and a cotyledon end 34. Referring back to FIG. 1, during conventional assembly of the manufactured seed 10, the plant embryo 20 is first inserted into the cavity before the fill material 30 is deposited. The fill material 30 is preferably, but not necessarily, deposited within the cavity 18 such that it substantially centers the plant embryo 20 within the cavity 18.

Figure 3:
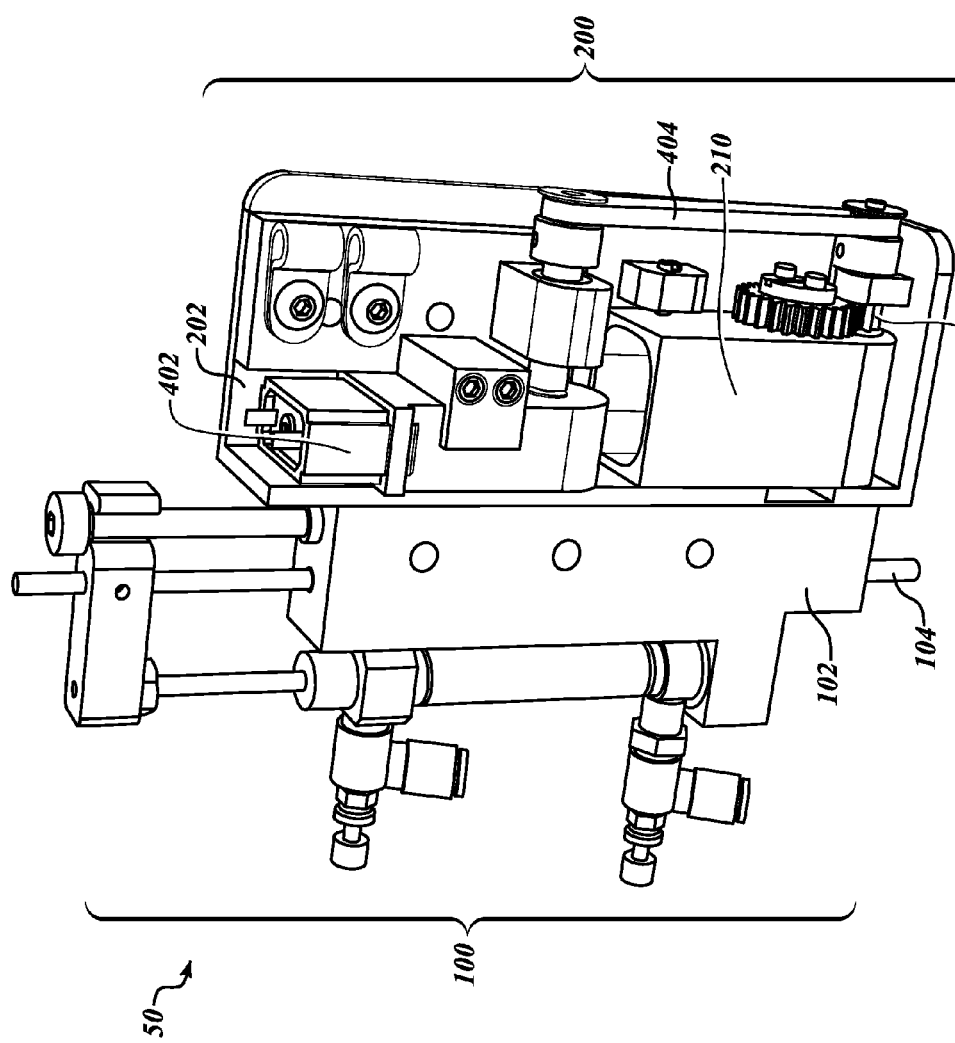
FIG. 3 is a front isometric view of an embryo insertion system according to embodiments of the disclosure.
Figure 4:
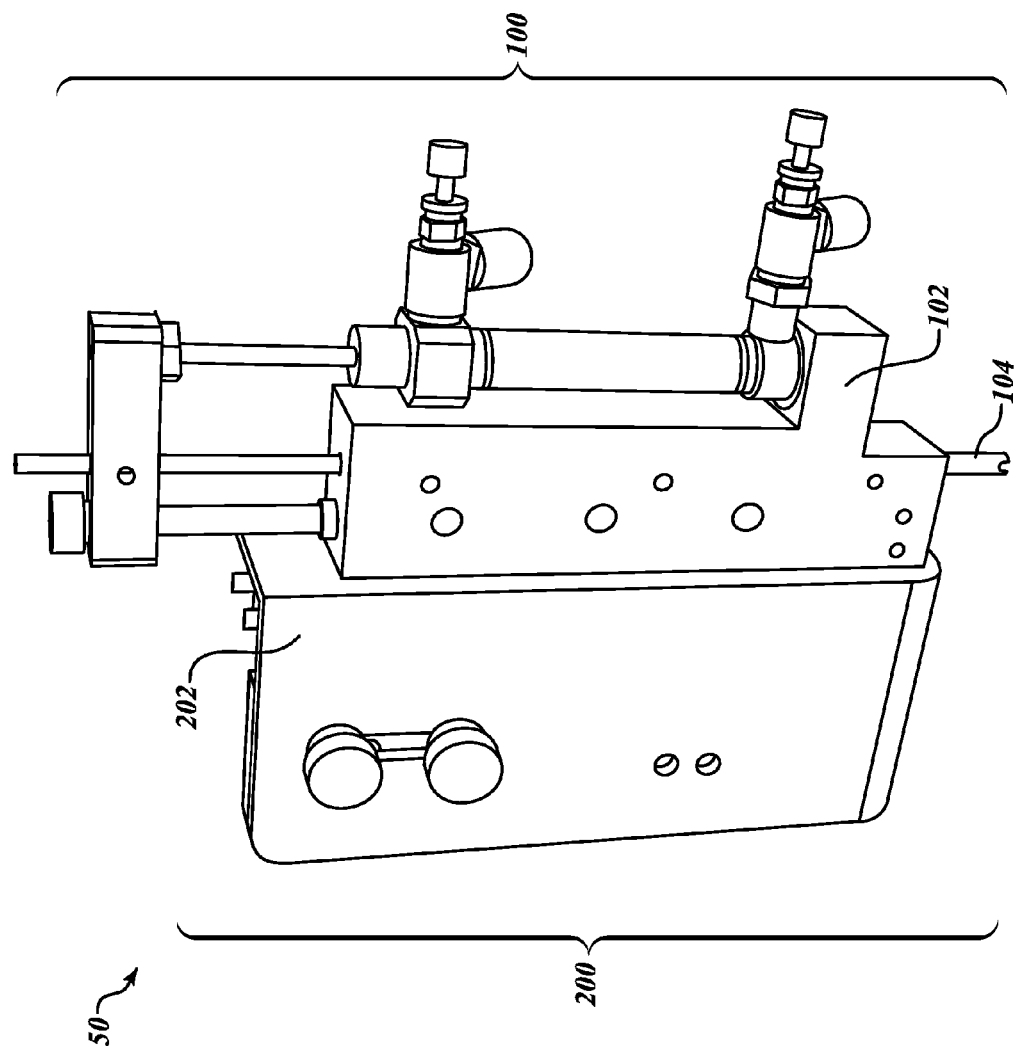
FIG. 4 is a back isometric view of an embryo insertion system according to embodiments of the disclosure.

In embodiments according to the disclosure, the plant embryo 20 and fill material 30 may be inserted in a single step. FIGS. 3 and 4 are isometric views of an embryo insertion system 50 according to embodiments of the disclosure. FIG. 3 is a front view and FIG. 4 is a back view. Referring to FIGS. 3 and 4, the embryo insertion system 50 comprises an embryo delivery assembly 100 and a fill material deposit assembly 200. In embodiments according to the disclosure, the embryo delivery assembly 100 and the fill deposit assembly 200 simultaneously insert a plant embryo 20 (as shown in FIG. 2) and fill material 30 (as shown in FIG. 1) into a cavity 18 of a manufactured seed 10 (as shown in FIG. 1).

The embryo insertion system 50 may be mounted on a frame (not shown) as part of a manufacturing system. In some embodiments, the embryo delivery assembly 100 may be arranged side-by-side with the fill material deposit assembly 200. The embryo delivery assembly may be housed in a first housing 102 that is operably connected to a second housing 202 for the fill material deposit assembly 200. In some embodiments the first housing 102 and the second housing 202 may be separate structures, which are attached in any manner known to a person of ordinary skill in the art. In other embodiments, the first housing 102 and the second housing 202 may be integrally manufactured as a single structure.

Figure 5:
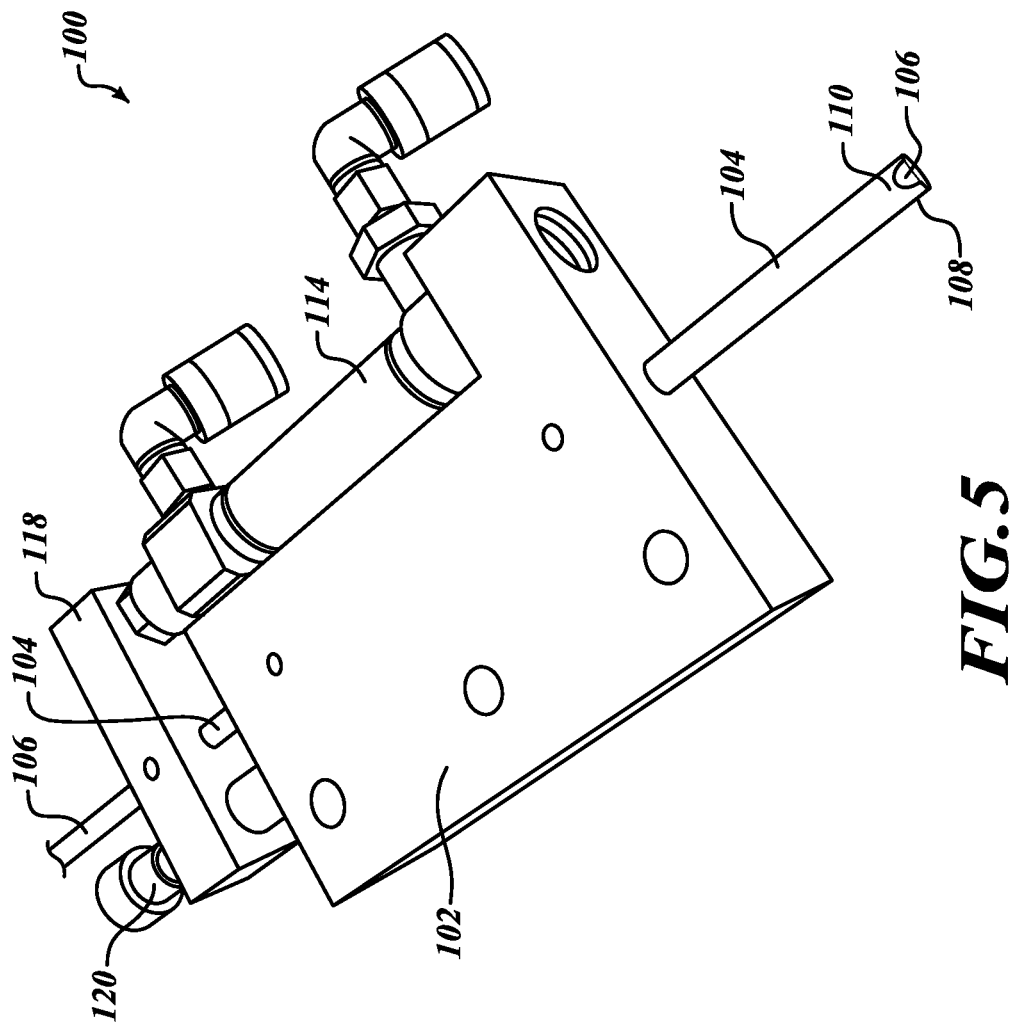
FIG. 5 is an isometric view of an embryo delivery assembly according to embodiments of the disclosure.

FIG. 5 is a detailed illustration of an embryo delivery assembly 100 according to embodiments of the disclosure. Embodiments of the embryo delivery assembly 100 include an insertion member 104 and a release assistance member 106. The insertion member 104 is shown arranged in the first housing 102. In some embodiments, the insertion member 104 and the release assistance member 106 may have a substantially cylindrical or tubular shape. In other embodiments, other shapes that would be suitable to a person of ordinary skill in the art may be used. The release assistance member 106 is moveable between an extended position (shown in FIGS. 5, 12, and 13), a retracted position (shown in FIG. 14), and various intermediate positions by an actuation assembly. The actuation assembly may include one or more air cylinders 114, an arm mechanism 118, and a shoulder screw 120. Other types of actuation assemblies that are known to a person of ordinary skill in the art may be substituted for the actuation assembly explicitly described. Further details about embryo delivery assemblies 100 suitable for use with systems and methods according to the disclosure are described, for example, in U.S. Patent Application Ser. No. 61/359,930 and U.S. Patent Application Ser. No. 61/359,917, the contents of which are hereby incorporated by reference.

Figure 6:
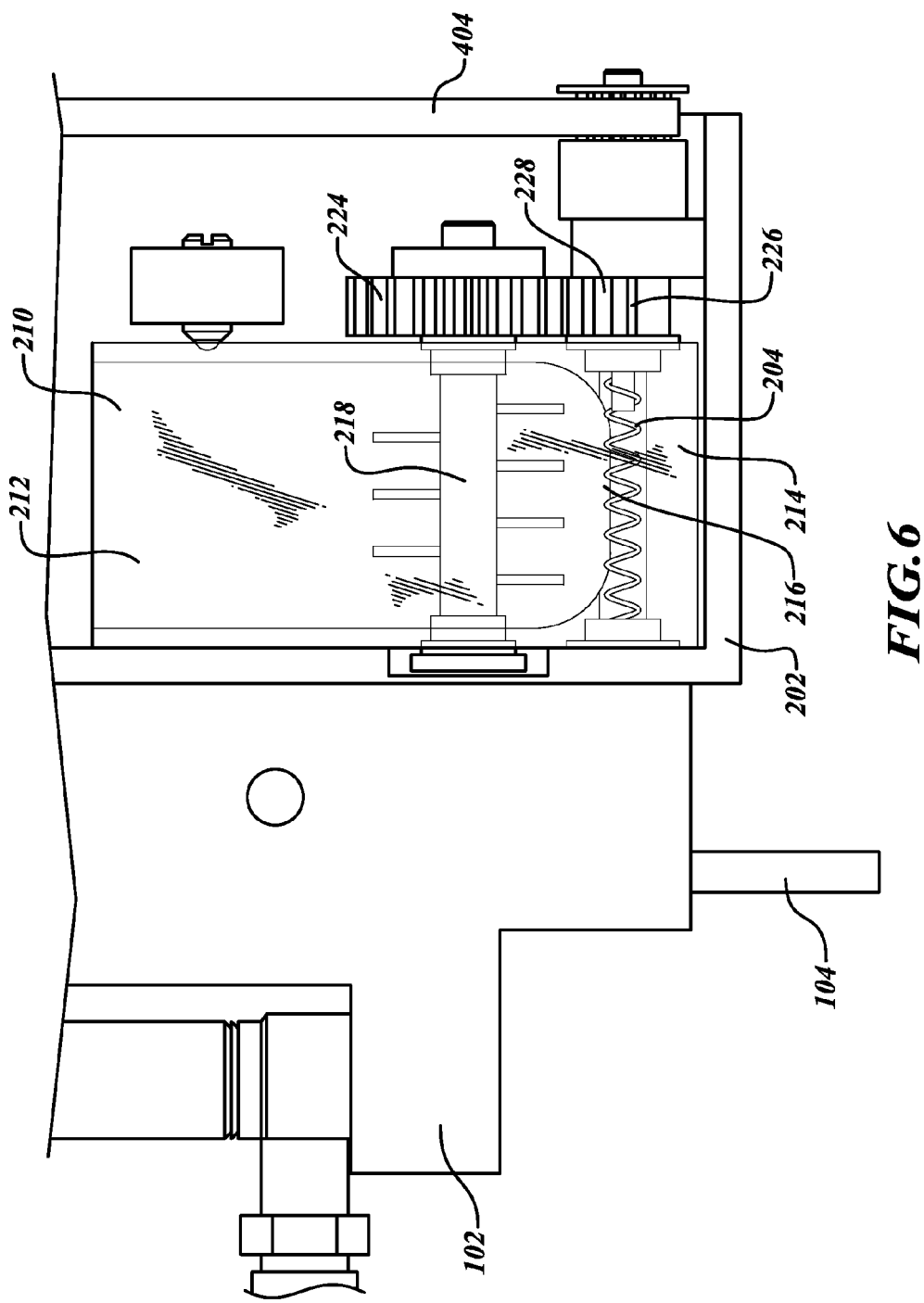
FIGS. 6 and 7 are side views of an embryo insertion system according to embodiments of the disclosure.
Figure 7:
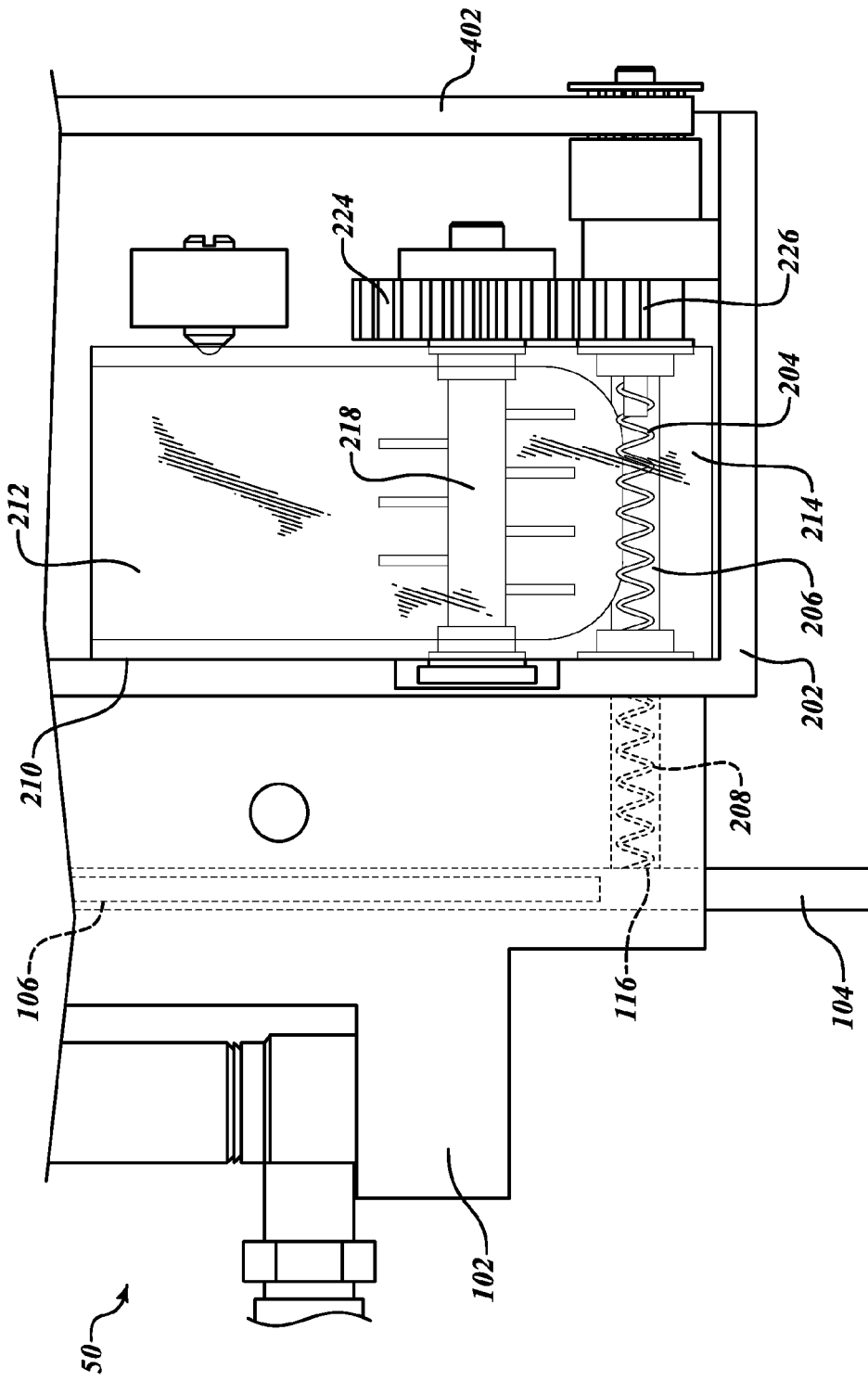
Figure 8:
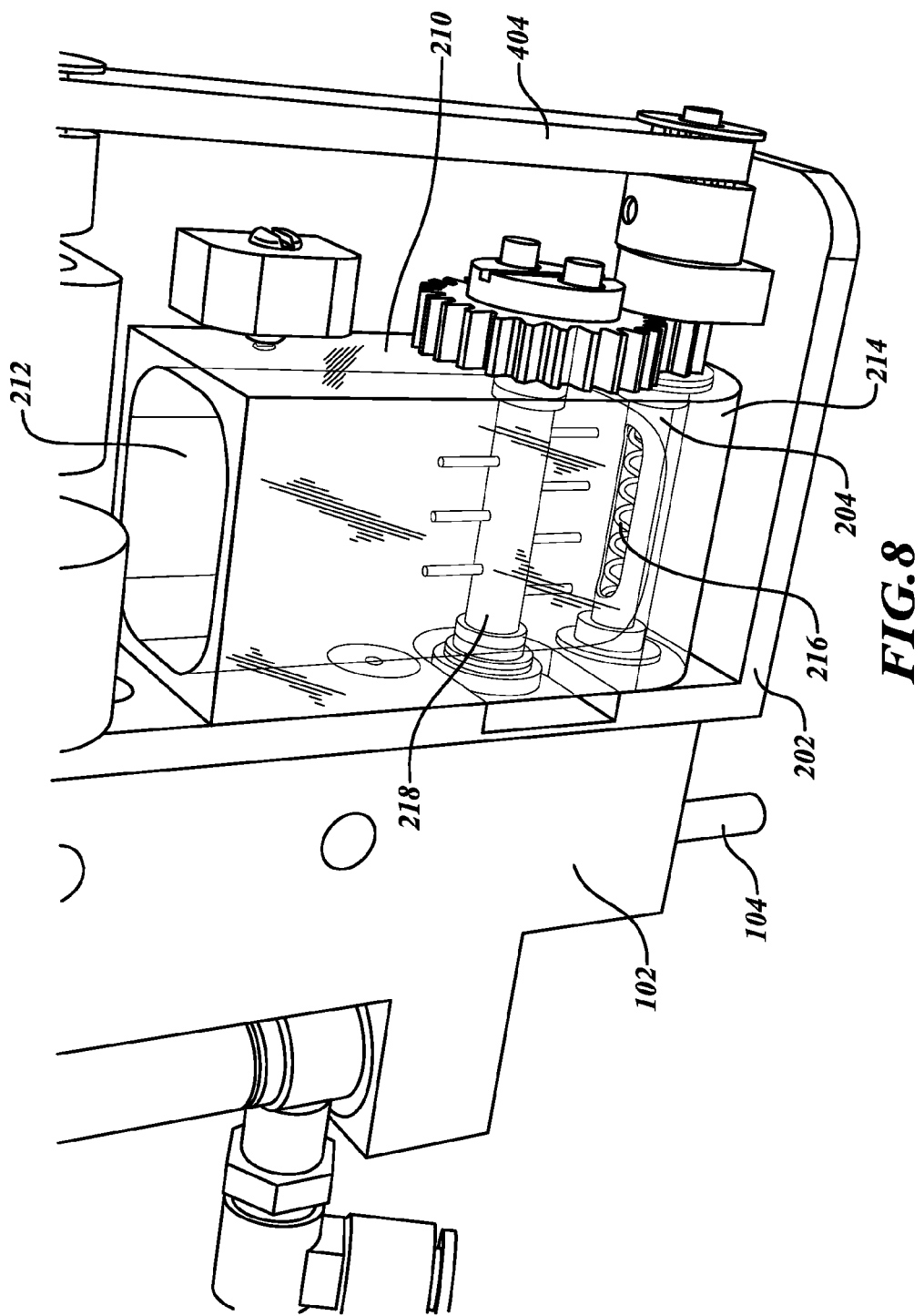
FIG. 8 is an isometric view of an embryo insertion system according to embodiments of the disclosure.
Figure 9:
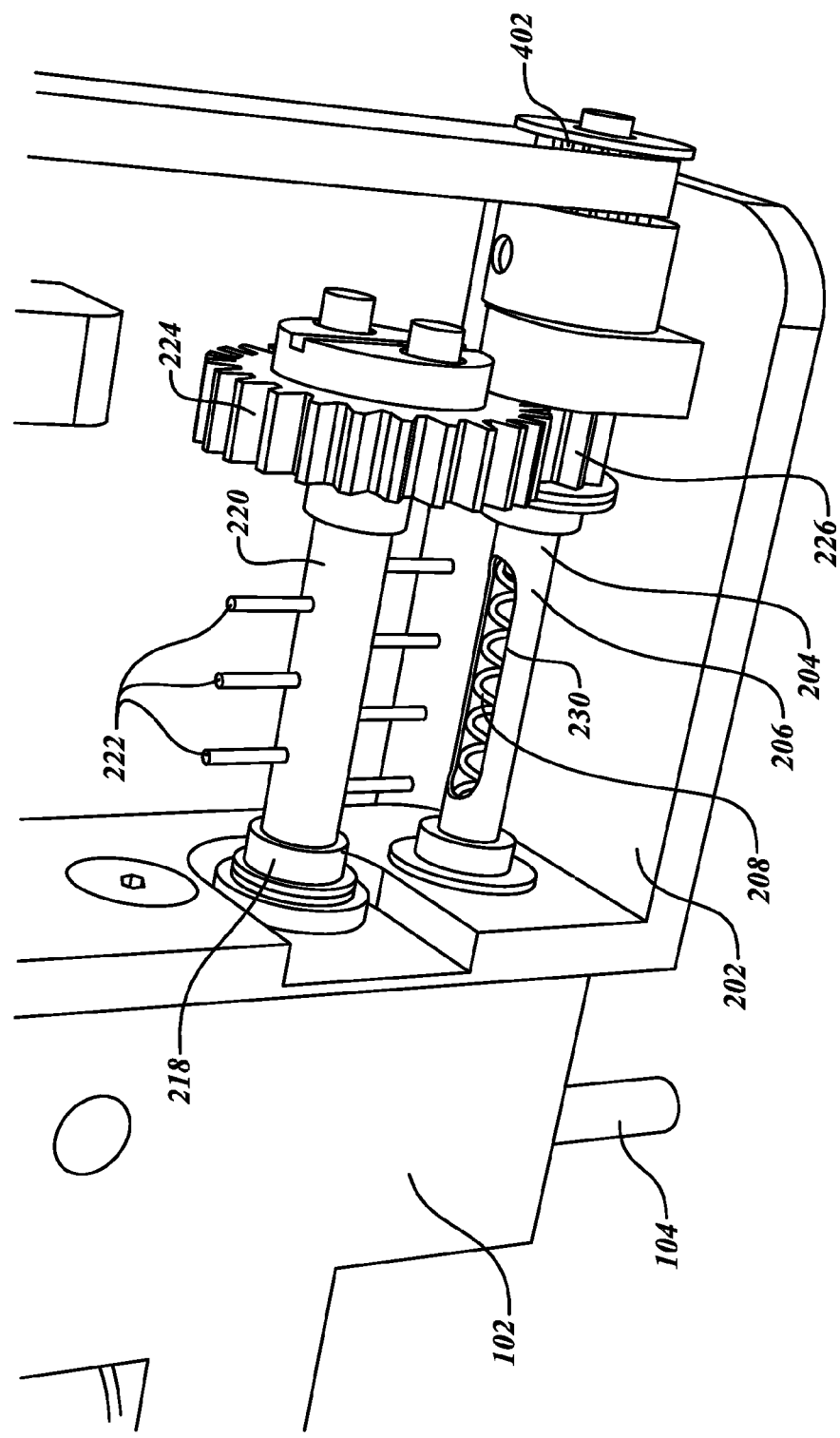
FIG. 9 is an isometric view of a portion of a fill material deposit assembly according to embodiments of the disclosure.

FIGS. 6-9 are detailed views of components of the fill material deposit assembly 200 in operable connection with a portion of the embryo insertion assembly 100 described above. FIGS. 6 and 7 are side views and FIGS. 8 and 9 are isometric views. Referring to all four figures, fill material deposit assemblies 200 according to embodiments of the disclosure include a fill material conveyance device 204 arranged to deliver fill material in a substantially perpendicular direction with respect to the insertion member 104. Referring to FIG. 7, the fill material conveyance device 204 may be connected to the insertion member via a port 116 located on the insertion member's side wall.

In some embodiments, the fill material conveyance device 204 includes a tubing 206 and a conveyor device 208 configured to push fill material 30 into the port 116. Some examples of suitable conveyor devices 208 are shown in FIGS. 10 and 11. As shown in FIG. 10, conveyor devices 208 according to embodiments of the disclosure may include a helically rotating auger 302. In other embodiments, a rotating drill bit 304 may be used as a conveyor device 208.

Further, other types of conveyor devices 208 that would be suitable to a person having ordinary skill in the art may be used. Referring back to FIG. 3, the fill material conveyance device 204 is connected to a drive mechanism 402 through a belt 404 or another connection mechanism. Accordingly, when the drive mechanism 402 is activated, the conveyor device 208 rotates.

Referring back to FIGS. 3, 6, and 8, the fill material deposit assembly 200 further includes a fill material containment device 210. The fill material containment device 210 may be any suitable container that is able to hold fill material 30. For example, in some embodiments the fill material containment device 210 may be rectangular shaped container manufactured to fit in the second housing 202. A person of ordinary skill in the art will appreciate that the particular shapes and configuration of the fill material containment device 210 is one illustration and that other shapes and configurations may be possible. The fill material containment device 210 may be detatchable from the first housing 102 and/or pivotable about a point 228 (see FIG. 6) to enable filling and/or emptying.

As shown in FIGS. 6 and 8, the fill material containment device 210 may have a reservoir portion 212 configured to store fill material 30 and a solid portion 214 positioned below the reservoir portion 212. In some embodiments, the solid portion 214 may be substantially rounded or otherwise shaped for easy removal from the second housing 202. The solid portion 214 may also have a channel 216 extending therein in a configuration that is substantially perpendicular to the insertion member 104. The channel 216 is sized to accommodate the fill material conveyance device 204. Referring to FIG. 9, the tubing 206 may have an opening 230 configured to permit the fill material 30 to fall from the fill material containment device 210 into the fill material conveyance device 204. In some embodiments, the solid portion 214 of fill material containment device 210 is integrally formed to define the opening 230.

In some applications, it may be useful to aerate, fluff, or otherwise separate the fill material 30 prior to insertion into the manufactured seed 10. Referring to FIGS. 6, 8, and 9, the fill material deposit assembly 200 may further include a fill material separation device 218 positioned above the fill material conveyance device 204. In some embodiments, the fill material separation device 218 may be positioned inside the reservoir portion 212 of the fill material containment device 210. As shown most clearly in FIG. 9, the fill material separation device 218 may include a central body 220 and one or more protruding elements 222. The central body 220 may be substantially cylindrical in shape. The elements 222 may have any shape suitable for separating fill material and may be arranged in any configuration on the central body 220 (e.g., fins, small cylinders). The fill material separation device 218 may be connected to a first gear 224 in operable connection with a second gear 226. The second gear 226 may be connected to the fill material conveyance device 204. Accordingly, when the drive mechanism 402 powers rotation of the second gear 226, the first gear 224 is engaged, thereby rotating the fill material separation assembly 218. A person of ordinary skill in the art will appreciate that in some embodiments, the specific configuration of this gear mechanism could be different. Further, the fill material separation device 218 may have a drive mechanism that is separate from the fill material conveyance device's drive mechanism.

Methods for using systems according to the disclosure for embryo insertion will now be described with reference to FIGS. 12-14. In an exemplary embodiment, the plant embryo 20 (e.g., a shown in FIG. 2) is transferred from a pick-up device 500 to the embryo delivery assembly 100. Pick-up devices 500 are generally known in the art and are typically used to pick up and orient embryos prior to insertion. Accordingly, the disclosure is not limited to use with a particular type of pick-up device. Although the Figures show the plant embryo 20 oriented with the cotyledon end 34 down with respect to the manufactured seed 10, other types of orientations may be used with systems and methods according to the disclosure. Examples of pick-up devices 500 that are suitable for use with embodiments of the disclosure are described, for example, in U.S. Patent Application Ser. No. 61/359,930 and U.S. Patent Application Ser. No. 61/359,917.

One problem encountered during handoff from the pick-up device 500 is that the plant embryos 20 often become stuck on the pick-up device 500 or damaged during transfer. Even if a plant embryo 20 is successfully transferred from the pick-up device 500, it may be damaged during insertion into the manufactured seed 10. Because plant embryos 20 are dissimilar in shape and size, it is difficult to design a single solution for delivering all types of embryos without damage.

Figure 12:
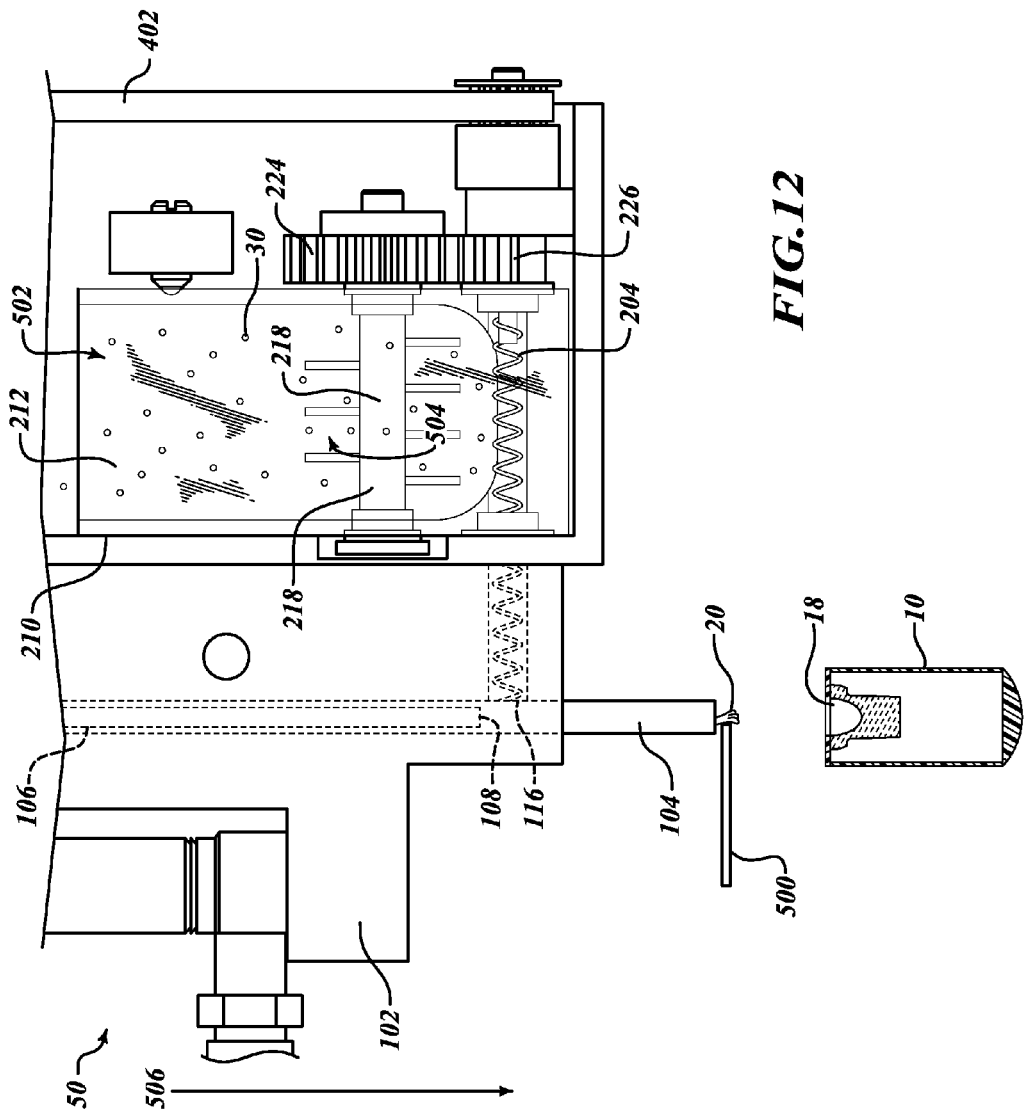
Figure 13:
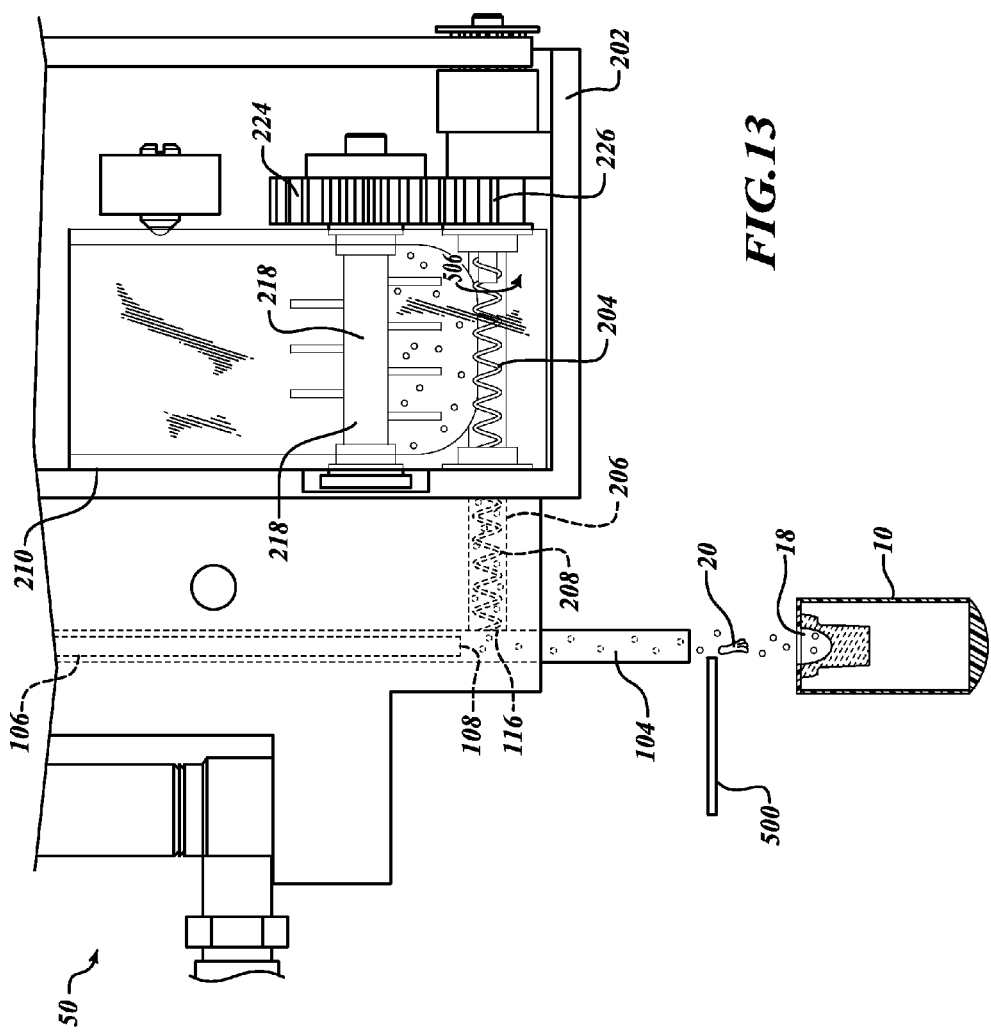

Referring to FIG. 12, fill material 30 may be loaded into the reservoir portion 212 of the fill material containment device 210 as shown by arrow 502. As the fill material 30 falls, the fill material separation device 218 may be activated, thereby rotating the fill material separation device 218 as shown by arrow 504 and the fill material conveyance device 204 as shown by arrow 506 (see FIG. 13). As a result, the fill material 30 is aerated, fluffed, or otherwise separated before it reaches the fill material conveyance device 204. According to embodiments of the disclosure, while the plant embryo 20 is connected to the pick-up device 500, the embryo insertion system 50 is lowered (as shown by arrow 506) so that the insertion member 104 surrounds the plant embryo 20. Because the insertion member 104 may have a notch (not shown) the pick-up device 500 can grasp the plant embryo 20 while the insertion member 104 surrounds it. During this stage, the release assistance member 106 is in the retracted position as shown in FIG. 12, the end 108 being located above the port 116.

After the plant embryo 20 is properly surrounded, the pick-up device 500 releases the plant embryo 20 so that it may fall into the cavity 18. Referring to FIG. 13, the fill material conveyance device 204 simultaneously delivers fill material 30 to the insertion member 104 via the port 116 so that it rains down on the plant embryo 20. In some applications, these steps alone may be sufficient to successfully place the plant embryo 20 into the cavity 18 of the manufactured seed 10. Additionally, a portion of the fill material 30 may also be deposited into the cavity 18 with the embryo. The pick-up device 500 may then be retracted.

In other applications, the plant embryo 20 may remain stuck on the pick-up device 500 or otherwise require additional assistance. In these cases, after the pick-up device 500 has been retracted, the release assistance member 106 may be transitioned from the retracted position shown in FIGS. 12 and 13 to an extended position as shown in FIG. 14. Even if the plant embryo 20 has been successfully deposited, movement of the release assistance member 106 may also be effective to ensure that the fill material 30 has been removed and is not clogging the insertion member 104.

Embodiments according to the disclosure are expected to aid in embryo insertion and delivery of fill material. Referring to FIG. 1, in some embodiments, the cavity 18 may be filled with enough fill material 30 so that the plant embryo 20 and the fill material 30 fill 100% of the cavity. In other embodiments, the cavity 18 may be partially filled so that additional fill material 30 may be added during a later step in the manufacturing process. Although not necessary, in some embodiments, additional fill material 30 may be added to the cavity as part of the manufacturing process.

From the foregoing, it will be appreciated that the specific embodiments of the disclosure have been described herein for purposes of illustration, but that various modifications may be made without deviating from the disclosure. For example, the specific configuration and geometry of the fill material containment device 204 may be modified based on the knowledge of a person having ordinary skill in the art. Aspects of the disclosure described in the context of particular embodiments may be combined or eliminated in other embodiments. For example, fill material deposit assemblies 200 according to the disclosure may include a fill material conveyance device 204 and a fill material containment device 210. In some embodiments, a fill material separation device 218 may or may not be included. Additionally, the specific configuration of the afore-mentioned components may be adjusted according to the practices of a person having ordinary skill in the art.

Further, while advantages associated with certain embodiments of the disclosure may have been described in the context of those embodiments, other embodiments may also exhibit such advantages, and not all embodiments need necessarily exhibit such advantages to fall within the scope of the disclosure. Accordingly, the invention is not limited except as by the appended claims.

We claim:

1. An embryo insertion method comprising:
    (a) aligning a pick-up device having a plant embryo loaded therein with a manufactured seed having a restraint such that the plant embryo is located above a cavity of the restraint;
    (b) lowering an embryo insertion system over the plant embryo loaded in the pick-up device such that an embryo insertion member of the embryo insertion system surrounds the plant embryo, wherein the embryo insertion member includes a notch adapted to receive the pick-up device when the embryo insertion member surrounds the plant embryo;
    (c) releasing the plant embryo from the pick-up device to thereby deposit the plant embryo in the cavity of the manufactured seed; and
    (d) depositing a fill material into the cavity via a fill material conveyance device;
       wherein steps (c) and (d) are performed concurrently.

2. The embryo insertion method of claim 1 wherein step (d) comprises:
    delivering the fill material from a fill material containment device to a port located on the insertion member via rotation of the fill material conveyance device.

3. The embryo insertion method of claim 2, further comprising the step of separating the fill material before the step of delivering the fill material from the fill material containment device to the port located on the insertion member.

4. The embryo insertion method of claim 3 wherein the step of separating the fill material is performed by a fill material separation device arranged inside the fill material containment device, the fill material separation device comprising a central rotating body having one or more protruding elements.

5. The embryo insertion method of claim 2 wherein the fill material conveyance device comprises a tubing and a rotating auger.

6. The embryo insertion method of claim 2 wherein the fill material is a powder.

7. The embryo insertion method of claim 2 wherein the fill material is charcoal, resins, zeolites, alumina, clay, diatomaceous earth, or silica gel.

8. The embryo insertion method of claim 1 wherein the embryo insertion system further comprises a release assistance member arranged inside the insertion member and the method further comprises the step of extending the release assistance member towards the plant embryo and contacting the plant embryo.

9. The embryo insertion method of claim 8, further comprising the step of repositioning the pick-up device to no longer be aligned with manufactured seed after releasing the plant embryo from the pick-up device and before extending the release assistance member towards the plant embryo and contacting the plant embryo.

* * * * *